(12) United States Patent
Lewellen et al.

(10) Patent No.: US 9,442,198 B2
(45) Date of Patent: *Sep. 13, 2016

(54) OPTICAL-INTERFACE PATTERNING FOR RADIATION DETECTOR CRYSTALS

(71) Applicant: University of Washington through its Center for Commercialization, Seattle, WA (US)

(72) Inventors: Thomas K. Lewellen, Port Ludlow, WA (US); William C. J. Hunter, Lynnwood, WA (US); Robert S. Miyaoka, Shoreline, WA (US); Lawrence MacDonald, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/692,617

(22) Filed: Apr. 21, 2015

(65) Prior Publication Data

US 2015/0226862 A1 Aug. 13, 2015

Related U.S. Application Data

(63) Continuation of application No. 13/504,480, filed as application No. PCT/US2010/054307 on Oct. 27, 2010, now Pat. No. 9,040,924.

(60) Provisional application No. 61/255,407, filed on Oct. 27, 2009.

(51) Int. Cl.
*G01T 1/20* (2006.01)
*A61B 6/03* (2006.01)
(Continued)

(52) U.S. Cl.
CPC ............ *G01T 1/2002* (2013.01); *A61B 6/037* (2013.01); *G01T 1/1642* (2013.01); *G01T 1/2018* (2013.01); *G01T 1/2023* (2013.01)

(58) Field of Classification Search
CPC ..................... G01T 1/2018; G01T 1/2002
See application file for complete search history.

(56) References Cited

U.S. PATENT DOCUMENTS 6,473,486 B2    10/2002  Hoffman
7,709,805 B2    5/2010   Burr
(Continued)

FOREIGN PATENT DOCUMENTS

CN    101248370 A    8/2008
WO    2009/136519 A1    11/2009

OTHER PUBLICATIONS

Chinese Office Action mailed Mar. 31, 2014, issued in corresponding Application No. CN 201080056301.6, filed Oct. 27, 2010, 16 pages.
(Continued)

*Primary Examiner* — Christine Sung
(74) *Attorney, Agent, or Firm* — Christensen O'Connor Johnson Kindness PLLC; Juan Zheng; Ryan Dodge (57) ABSTRACT

A radiation detector is disclosed that includes a scintillation crystal and a plurality of photodetectors positioned to detect low-energy scintillation photons generated within the scintillation crystal. The scintillation crystals are processed using subsurface laser engraving to generate point-like defects within the crystal to alter the path of the scintillation photons. In one embodiment, the defects define a plurality of boundaries within a monolithic crystal to delineate individual detector elements. In another embodiment, the defects define a depth-of-interaction boundary that varies longitudinally to vary the amount of light shared by neighboring portions of the crystal. In another embodiment the defects are evenly distributed to reduce the lateral spread of light from a scintillation event. Two or more of these different aspects may be combined in a single scintillation crystal. Additionally, or alternatively, similar SSLE defects may be produced in other light-guiding elements of the radiation detector.

10 Claims, 6 Drawing Sheets

(51) Int. Cl.
*G01T 1/164* (2006.01)
*G01T 1/202* (2006.01)

(56) References Cited

U.S. PATENT DOCUMENTS

| | | |
|---|---|---|
| 7,818,047 B2 | 10/2010 | Tumer |
| 8,779,371 B2 | 7/2014 | Moriya |
| 2004/0262526 A1 | 12/2004 | Corbeil |
| 2005/0023733 A1 | 2/2005 | Burr |
| 2006/0202125 A1 | 9/2006 | Suhami |
| 2009/0224158 A1 | 9/2009 | Haselman |
| 2010/0012846 A1 | 1/2010 | Wang |

OTHER PUBLICATIONS

International Search Report and Written Opinion mailed Jun. 23, 2011, issued in corresponding International Application No. PCT/US2010/054307, filed Oct. 27, 2010, 6 pages.

Moriya, T., et al., "Development of PET Detectors Using Monolithic Scintillation Crystals Processed With Sub-Surface Laser Engraving Technique," Proceedings of the IEEE 2009 Nuclear Science Symposium and Medical Imaging Conference, Orlando, Fla., Oct. 25-31, 2009, pp. 3560-3564. Abstract.

Fig. 7 ined. For example, organic scintillators may be useful for some applications, e.g., fast neutron detection.

OPTICAL-INTERFACE PATTERNING FOR RADIATION DETECTOR CRYSTALS

CROSS-REFERENCE TO RELATED APPLICATION

This application is a continuation of U.S. patent application Ser. No. 13/504,480, filed Jun. 5, 2012, which is a National Stage of International Application No. PCT/US2010/054307, filed Oct. 27, 2010, which claims the benefit of U.S. Provisional Application No. 61/255,407, filed Oct. 27, 2009, the disclosure of each of which is hereby incorporated by reference in its entirety.

STATEMENT OF GOVERNMENT LICENSE RIGHTS

This invention was made with Government support under EB002117 awarded by National Institutes of Health, National Institute of Biomedical Imaging and Bioengineering. The Government has certain rights in the invention.

BACKGROUND

Scintillation crystal radiation detection systems rely on high-energy photons, such as gamma rays, interacting with a scintillation material in a Compton scattering or photoelectric interaction. The scintillation event produces a large number of lower-energy photons that are more readily detected using a photodetector, for example, a photomultiplier tube, silicon photomultiplier, or the like.

Exemplary scintillation crystals include NaI(Tl) (thallium-doped sodium iodide), BGO (bismuth germinate), LSO (lutetium oxyorthosilicate), GSO (gadolinium orthosilicate), LYSO (cerium-doped lutetium yttrium orthosilicate), LuAP (lutetium aluminum perovskite), LGSO (Lu0.4Gd1.6Si05: 22.0 mol % Ce), LaBr3 (lanthanum bromide) and the like. For example, when BGO interacts with high-energy radiation, such as gamma-rays or x-rays, it emits a green fluorescent light with a peak wavelength of 480 nm. BGO is used for a wide range of applications in high-energy physics, nuclear physics, space physics, nuclear medicine, geological prospecting, and other industries. LYSO crystal has the advantages of high light output and density, quick decay time, excellent energy resolution, and moderate cost. These properties make LYSO a good candidate for a range of detection applications in nuclear physics and nuclear medicine, which require improved timing and energy resolution.

In typical scintillation crystals used in positron emission tomography (PET), for example, an incident gamma photon having a nominal energy of 511 keV interacts in the scintillation crystal to produce tens of thousands of low-energy (e.g., visible wavelength) photons (~1 eV) in a very short flash or scintillation event. The number of scintillation photons produced in the crystal is proportional to the energy deposited by the photon.

The lower-energy scintillation photons are then detected with photodetectors that are typically placed in an array on one side, or on opposite sides of the scintillation crystal. Typical photodetectors include photomultiplier tubes (PMT), avalanche photodiodes (APDs), Si-PIN photodiodes, silicon drift photodiodes, and silicon photomultipliers (SiPM). The radiation detector is configured to identify a high-energy photon interaction by detecting the low-energy photons produced in the scintillation event, and to determine the location of the scintillation event within the scintillation crystal (preferably, in three spatial dimensions), the time of the scintillation event, and the total energy of the event.

Positron Emission Tomography (PET)

Although radiation detectors in accordance with the present invention are contemplated to have applications in several different fields, ranging from cosmological imaging to the detection of radioactive materials, a particular application in the field of medical imaging will be described in some detail to assist the reader in understanding the description of the invention that will follow.

Positron emission tomography (PET) is a medical imaging modality that takes advantage of radioactive decay to measure metabolic activities inside a living organism. A PET imaging system comprises three main components, indicated schematically in FIG. 1, a radioactive tracer that is administered to the subject to be scanned, a scanner that is operable to detect the location of radioactive tracer (indirectly as discussed below), and a tomographic image processing system.

Figure 1:
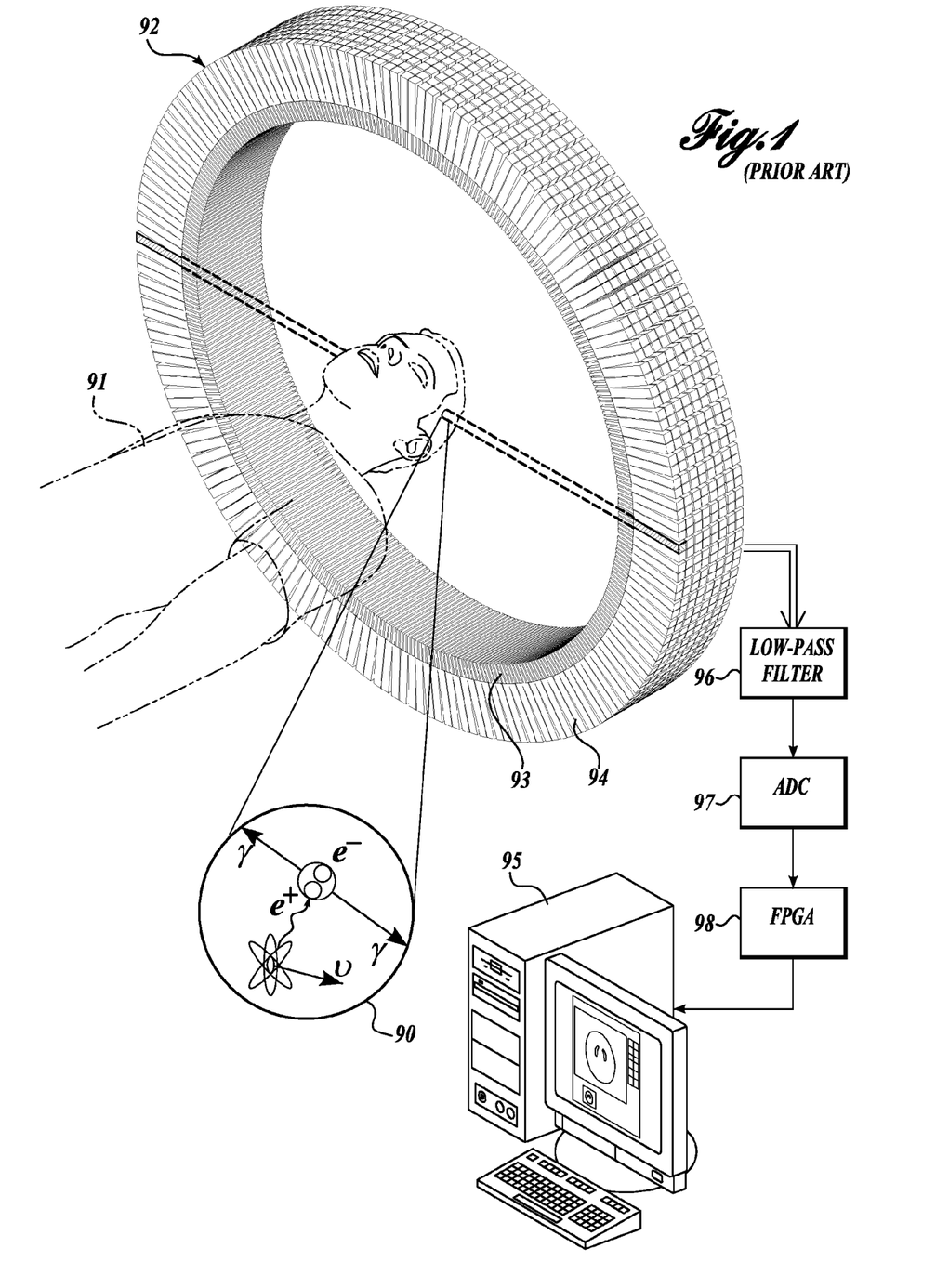
FIG. 1 is an environmental view showing a PET scanner system.

The first step is to produce and administer a radioactive tracer 90, comprising a radioactive isotope and a metabolically active molecule. The tracer 90 is injected into the body to be scanned 91. After allowing time for the tracer 90 to concentrate in certain tissues, the body 91 is suitably positioned inside the scanner 92. The radioactive decay event for tracers used in PET studies is positron emission. An emitted positron travels a short distance in the body tissue until it interacts with an electron. The positron-electron interaction is an annihilation event that produces two 511 KeV antiparallel photons. The scanner 92 is adapted to detect the pair of photons from the annihilation event simultaneously.

The scanner 92, the second component of PET system, includes a ring of sensors that detect the 511 KeV photons, and front-end electronics that process the signals generated by the sensors. As discussed above, the scintillators 93 converts the 511 KeV high-energy photons into many lower-energy photons, typically visible light photons. The photodetectors (e.g., PMT, SiMP or APD) 94 detect the visible light photons and generate a corresponding electrical pulse. The pulses are processed by front-end electronics to determine the parameters or characteristics of the pulse (e.g., energy, timing). The front-end electronics may include, for example, one or more low-pass filters 96, analog-to-digital converters 97, and field programmable gate arrays 98. The sensors typically comprise scintillators 93 and photodetectors 94.

The data is sent from the front-end electronics to a host computer 95 that performs tomographic image reconstruction to turn the data into a 3-D image.

A 511 KeV photon has a substantial amount of energy and will pass through many materials, including body tissue. While this typically allows the photon to travel through and exit the body, the high-energy photons are difficult to detect. Photon detection is the task of the scintillator 93. The scintillator 93 absorbs or otherwise interacts with high-energy photons and emits a relatively large number of lower-energy photons, typically visible light photons. The scintillator 93 can be made from various materials, including plastics, organic and inorganic crystals, and organic liquids. Each type of scintillator has a different density, index of refraction, timing characteristics, and wavelength of maximum emission. For convenience, in the present application scintillators will sometimes be referred to as "crystals," although other suitable scintillator materials are also contemplated. For purposes of this application "scintillator crystals" is defined to encompass any suitable scintillation material.

In general, the density of the scintillator determines how well the material stops the high-energy photons. The index of refraction of the scintillator crystal and the wavelength of the emitted light affect how easily light can be collected from the crystal. The wavelength of the emitted light also needs to be matched with the device that will turn the light into an electrical pulse (e.g., the PMT) in order to optimize the efficiency. The scintillator timing characteristics determine how long it takes the visible light to reach its maximum output (rise time) and how long it takes to decay (decay time). The rise and decay times are important because the longer the sum of these two times, the lower the number of events a detector can handle in a given period, and thus the longer the scan will take to get the same number of counts. Also, the longer the timing characteristics, the greater the likelihood that two events will overlap (pile-up), which can result in lost data.

Attached to the scintillator 93 are electronic devices that convert the visible light photons from the scintillator 93 into electronic pulses. A PMT is a vacuum tube with a photocathode, dynodes, and an anode that has high gains to allow very low levels of light to be detected. APDs are a semiconductor version of the PMT, but with significantly lower gain characteristics. SiPMs comprise an array of semiconducting photodiodes that operate in Geiger mode so that when a photon interacts and generates a carrier, a short pulse of current is generated. In an exemplary SiPM, the array of photodiodes comprises about 103 diodes per $mm^2$. All of the diodes are connected to a common silicon substrate so the output of the array is a sum of the output of all of the diodes. The output can therefore range from a minimum wherein one photodiode fires to a maximum wherein all of the photodiodes fire. This gives theses devices a linear output even though they are made up of digital devices.

In conventional PET detectors the scintillators 93 comprise discrete crystals arranged in a two-dimensional planar array, and then arranged into a ring as shown in FIG. 1. The photodetectors 94 for detecting the flashes of scintillation light are typically positioned adjacent the back surface of each individual crystal. The signals from the photodetectors are analyzed to estimate the x-y location of the scintillation event, to estimate the depth of interaction (i.e., z-location), to determine the time of the interaction, and to estimate the total energy deposited in the scintillator. However, given the small crystal cross-sections required to obtain very high resolution, discrete crystal designs are typically expensive, have low packing fraction, reduced light collection, and are labor intensive to build.

The present inventors have researched and developed new and advanced detectors for PET scanners. For example, *cMiCE: a high resolution animal PET using continuous LSO with a statistics based positioning scheme*, J. Joung, R. S. Miyaoka, T. K. Lewellen, Nuclear Instruments & Methods in Physics Research A 489 (2002) 584-598 (Elsevier), which is hereby incorporated by reference in its entirety, a continuous miniature crystal element (cMiCE) detector for small animal scanners is discussed. See also, U.S. Patent Application Publication No. 2010/0044571, which is also hereby incorporated by reference in its entirety.

In another example, *New Directions for dMiCE—Depth-of-Interaction Detector Design for PET Scanners*, T. K. Lewellen et al., IEEE Nucl Sci Symp Conf Rec (2007); 5:3798-3802, which is hereby incorporated by reference in its entirety, a novel depth-of-interaction (DOI) detector design based on light sharing between pairs or quadlets of crystals is discussed. See also, PCT Application Publication No. WO 2010/048363, which is also hereby incorporated by reference in its entirety.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A radiation detector is disclosed having a transparent scintillator block, which is modified using subsurface laser engraving to produce a plurality of internal defects within the block. The internal defects are precisely configured to alter the path of the low-energy scintillation photons. A plurality of photodetectors configured to detect the scintillation photons from scintillation events occurring in the block, and to generate an output signal. A computer system is configured to receive the output signals from the photodetectors for calculating the location of the scintillation event.

In an embodiment of the radiation detector the scintillation block is formed from thallium-doped sodium iodide, bismuth germinate, lutetium oxyorthosilicate, gadolinium orthosilicate, or cerium-doped lutetium yttrium.

In an embodiment of the radiation detector the plurality of photodetectors are photomultiplier tubes, avalanche photodiodes, or silicon photomultipliers.

In an embodiment of the radiation detector the scintillator block is a monolithic crystal, and the internal defects define a plurality of reflective walls that define boundaries segmenting the monolithic crystal into a rectangular array of scintillator elements.

In an embodiment of the radiation detector the scintillator block is a monolithic crystal with the array of photodetectors disposed on a first face of the crystal, and further the internal defects are distributed evenly throughout the crystal.

In an embodiment of the radiation detector the scintillator block defines a depth-of-interaction detector comprising a first portion with a photodetectors at a first end of the crystal element and a second portion with a second photodetectors at the first end of the crystal element, and the plurality of internal defects are disposed along a transverse plane that delineates the first portion of the depth-of-interaction detector from the section portion. The internal defects may define a triangular barrier and/or may be varied in density in the longitudinal direction.

In an embodiment of the radiation detector, a transparent light guide is disposed between the scintillator block and the plurality of photodetectors.

A scintillator for a radiation detector is disclosed, comprising a monolithic block of scintillation material having a plurality of subsurface laser engraved defects configured to interact with visible-wavelength photons produced in a scintillation event occurring in the scintillator.

In an embodiment of the scintillator the plurality of subsurface laser engraved defects define a grid of internal optical barriers that extend through a thickness of the scintillator, dividing the scintillator into a regular array of rectangular scintillator elements.

In an embodiment of the scintillator, the plurality of subsurface laser engraved defects define a depth-of-interaction optical boundary for each of the scintillator elements that extends partially through the scintillator element along a plane, wherein the depth-of-interaction optical boundary is triangular.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

We propose a novel application for subsurface laser engraving (SSLE), wherein SSLE is used to produce point-like defects in interior regions of an optical element such as a scintillation crystal. The defects are configured to control the transmission of low-energy photons within the optical device. For example, and as discussed in more detail below, an array of point defects produced by SSLE can serve as a reflective optical boundary or interface in an optical element, such as a scintillator, light guide, or lens. The pattern and density of the point defects and the characteristics of individual point defects determined by the SSLE process can be used to control the transport and/or distribution of light in the optical element. Furthermore, these properties of the point-defect pattern can vary as a function of position to make light transport non-stationary over the interface. Alternatively or in addition, a distribution of point defects introduced through the volume of an optical element can be used to reduce the lateral spread of the flash of scintillation photons. The defects produced by SSLE in the optical element may be produced to provide high efficiency reflection of photons, such that the light may be redirected in the optical element with relatively low loss (absorption) of photons.

Subsurface laser engraving is the process of creation or generation of two-dimensional or three-dimensional patterns within an optically clear material (e.g., glass, crystal or plastic) using a focused laser. The transparency of the material minimizes the attenuation and distortion of the laser. The lateral position of a pulsed laser beam is typically controlled by pairs of coordinated mirrors or right prisms (see, for example, U.S. Pat. No. 7,371,596, which is hereby incorporated by reference in its entirety). In SSLE, the depth of focus may be controlled by an actuated focusing element. Energy deposition by the pulsed laser at the focal spot causes rapid local heating, melting, and/or stress, which results in a relatively small or point-like defect, for example, a micro crack. Material properties at the point-like defect such as dopant diffusion, oxidation, crystallization, grain boundaries, fracturing, and so forth may be altered from that of the surrounding bulk material.

With careful generation and placement of the defects created by SSLE, the defects may be spatially constrained even in brittle scintillation crystals. For example, if the size of the defect is small compared to the distance to the boundary or another defect, then stress-induced fractures will not propagate far beyond the heated volume. The defect size depends on the size of the focal spot, on the rate of energy deposition and diffusion, and on the laser wavelength. In this manner, SSLE has been used to produce images in optically clear materials to be used as souvenirs or promotional items. A general process of SSLE is disclosed in U.S. Pat. No. 5,206,496, which is hereby incorporated by reference in its entirety. See also U.S. Pat. Nos. 6,969,820; 6,426,480; and 4,843,207.

Figure 2:
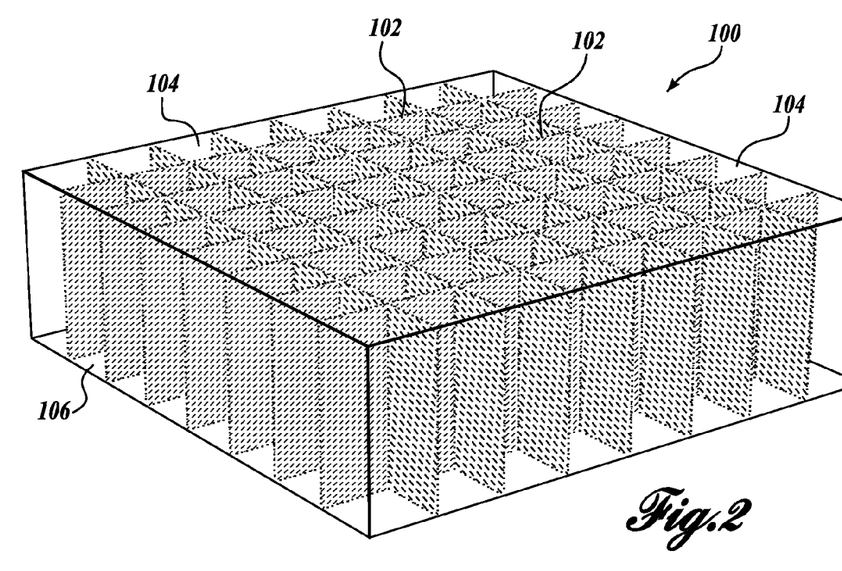
FIG. 2 is a perspective view of a monolithic scintillation block segmented into an eight by eight array of elements by a plurality of subsurface laser engraved walls or barriers that define reflective internal surfaces.

Monolithic Scintillator Block with Internal Optical Boundaries Defined Using SSLE In a first embodiment shown in FIG. 2, a scintillator block 100 is formed from a monolithic block of scintillation material, for example, a LYSO crystal measuring 49.6 mm×49.6 mm×15 mm. A grid of optical barriers 102 are formed through the block 100, each barrier formed as a planar array of defects etched using SSLE. As shown in FIG. 2, in this embodiment the optical barriers 102 are perpendicular to the upper and lower faces of the block 100, and are configured to define a regular array of 64 transparent crystal elements 104. Each of the defined crystal scintillator elements 104 are approximately 3.1 mm×3.1 mm×15 mm.

Therefore, the scintillator block 100 defines a square 8×8 array of scintillator elements 104, having substantially reflective boundaries defined by the SSLE-generated optical barriers 102 therebetween. In addition, the outer perimeter wall 106 of the block 100 is typically provided with a reflective barrier, which may be formed, for example, by laser engraving the surface of the block 100, or by conventional application of a reflective material. Although a square 8×8 array is shown in this exemplary embodiment, it will be appreciated that other array sizes may alternatively be used, including, for example, a 16×16 array, an 8×16 array, non-square arrays, etc. Also, although uniform rectangular scintillator elements 104 are shown, it will be readily apparent that with SSLE it is straightforward and contemplated by the present invention that the scintillator elements may be advantageous in some situations to define an array of scintillator elements having different sizes in an array, and/or with different shapes, including, for example, trapezoidal elements.

Figure 3:
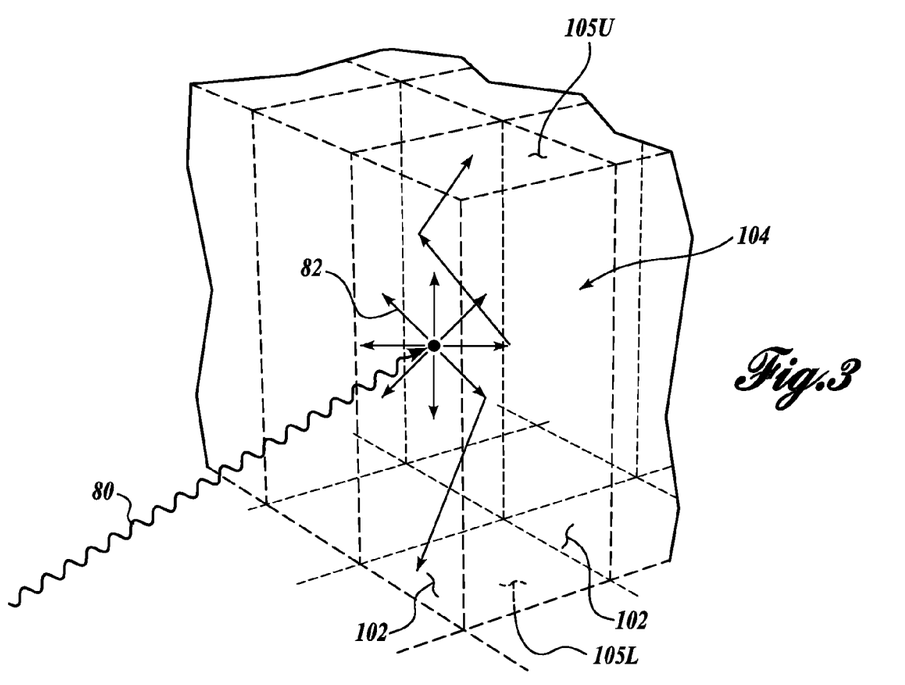
FIG. 3 is a perspective view of a crystal element from the monolithic scintillation block shown in FIG. 2, and showing diagrammatically a scintillation event.

Advantageously, the scintillator block 100 comprises a single unitary block, rather than a conventional assembly of individual elements. Because of the barriers 102 defined within the block 100, the crystal elements 104 act substantially as separate scintillator blocks. FIG. 3 illustrates a fragmentary portion of the block 100, including an individual crystal element 104. A gamma ray 80 enters the crystal element 104 and interacts by either Compton scattering or photoelectric interaction to produce an omnidirectional flash of scintillation photons 82. Some of the photons will be directed towards an upper face 105U or a lower face 105L of the crystal element 104, to be detected by a photodetector (not shown). Most of the photons having a more lateral trajectory will reflect one or more times from the optical boundary 102 and eventually exit the crystal element 104 from either the upper face 105U or the lower face 105L. It is contemplated that some of the photons may pass through gaps in the optical boundary 102 and reflect from optical boundaries 102 in neighboring crystal elements 104, to be detected by neighboring photodetectors. In such cases, the signals from multiple neighboring photodetectors may be analyzed collectively to calculate the position, timing, and energy of a particular scintillation event.

The disclosed construction of the scintillator block 100 provides several advantages over the prior art. For example, only a single block of scintillation material (e.g., LYSO) must be fabricated to produce a plurality of crystal elements 104, greatly reducing the time and expense associated with manufacturing and assembling a large number separate blocks. In addition, no additional light blocking or light reflecting material need be provided and assembled between separate blocks.

The disclosed construction also eliminates the dead zones created by reflective materials disposed between individual blocks in prior art constructions, which do not produce scintillation photons. For example, in prior art scintillation blocks formed from a plurality of individual blocks assembled with a reflective material therebetween, the reflective material is not a scintillation material, and would not produce flashes of light (scintillation photons) if a gamma ray, for example, interacts with the reflective material. Gamma rays that interact with the reflective material would therefore not be detected. As the design of radiation detectors move towards smaller individual scintillator block sizes (in order to increase image resolution) the dead regions defined by the reflective material will become more significant. In the block 100 defined above, however, the entire block is LYSO, and will therefore produce a flash of light when a Compton or photoelectric interaction with a gamma ray 80 occurs.

Depth of Interaction Detector Design

In *New Directions for dMiCE—Depth-of-Interaction Detector Design for PET Scanners* referenced above, a depth-of-interaction scintillation detector is disclosed wherein a pair of scintillation crystals are arranged side-by-side, and a shaped reflector is provided covering a portion of the interface between the two scintillation crystals. The reflector may be triangular shaped, for example. As discussed in detail in the referenced paper, the paired crystals have a transparent region therebetween, and will therefore "share" a portion of the light produced in a scintillation event in either of the crystals. Photodetectors are provided for at least one end of both crystals, and the amount of light detected for both crystals can be analyzed. By comparing the detected signals from both crystals, an estimate depth-of-interaction (the longitudinal position of the scintillation event) can be calculated. In prior embodiments of this depth-of-interaction detector, the two crystals and the reflector are formed separately, and the three components are assembled with an adhesive.

Figure 4:
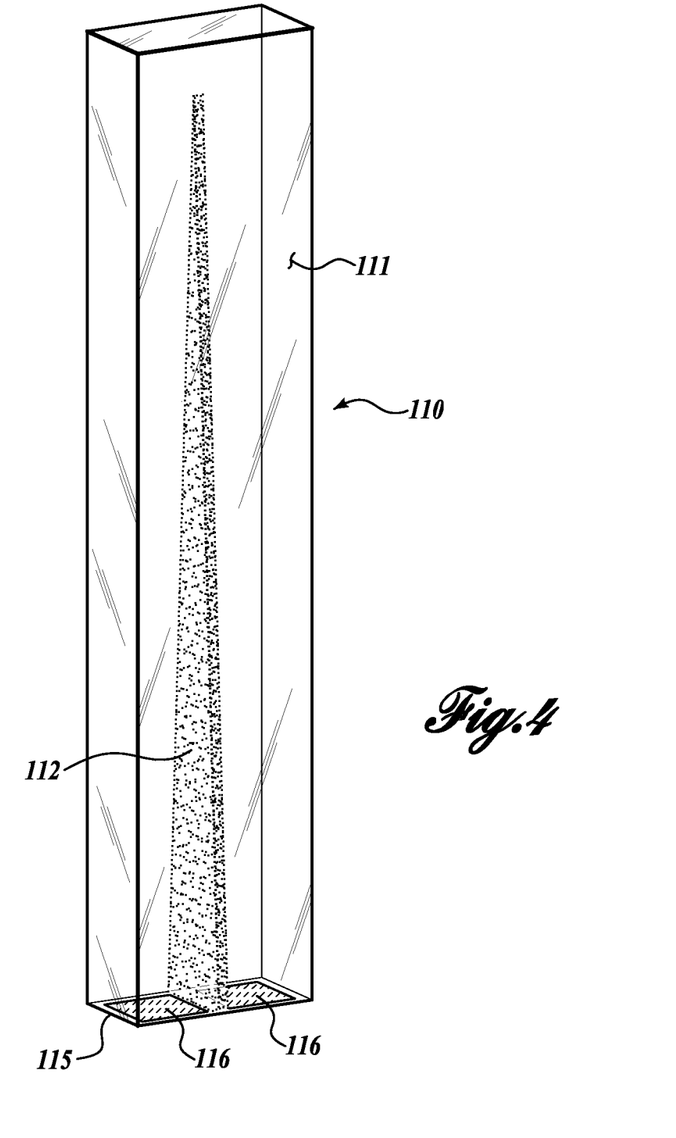
FIG. 4 is a perspective view of a depth-of-interaction monolithic crystal pair with an internal reflective barrier or feature formed by subsurface laser engraving.

FIG. 4 illustrates an exemplary depth-of-interaction detector 110, constructed in accordance with the present invention, and comprising a monolithic crystal 111. In this embodiment, the monolithic crystal 111 is processed using SSLE to define an internal boundary 112 comprising an array of spaced point-like defects generally along a transverse plane. A pair of photodetectors 116 are provided adjacent a bottom face 115 of the crystal 111. The internal boundary 112 is generally triangular, extending across the width of the crystal at the bottom face 115 and tapering as it extends upwardly most of the way to the top of the crystal 111. Although a triangular boundary 112 is shown, other shapes having a portion that extend only part of the transverse plane may be alternatively used, and are contemplated.

It will be appreciated that the disclosed configuration is simpler to construct than similar prior art depth-of-interaction crystal pairs that are assembled from two separate crystals. Therefore, this construction shares the advantages discussed above. An additional advantage for this type of depth-of-interaction monolithic crystal is that the non-blocked portion of the crystal along the plane defined by the triangular boundary 112 does not include a joint or interface between two separate crystals. Therefore, the present construction will improve the light-sharing between the two sides of the crystal 111.

Figure 5:
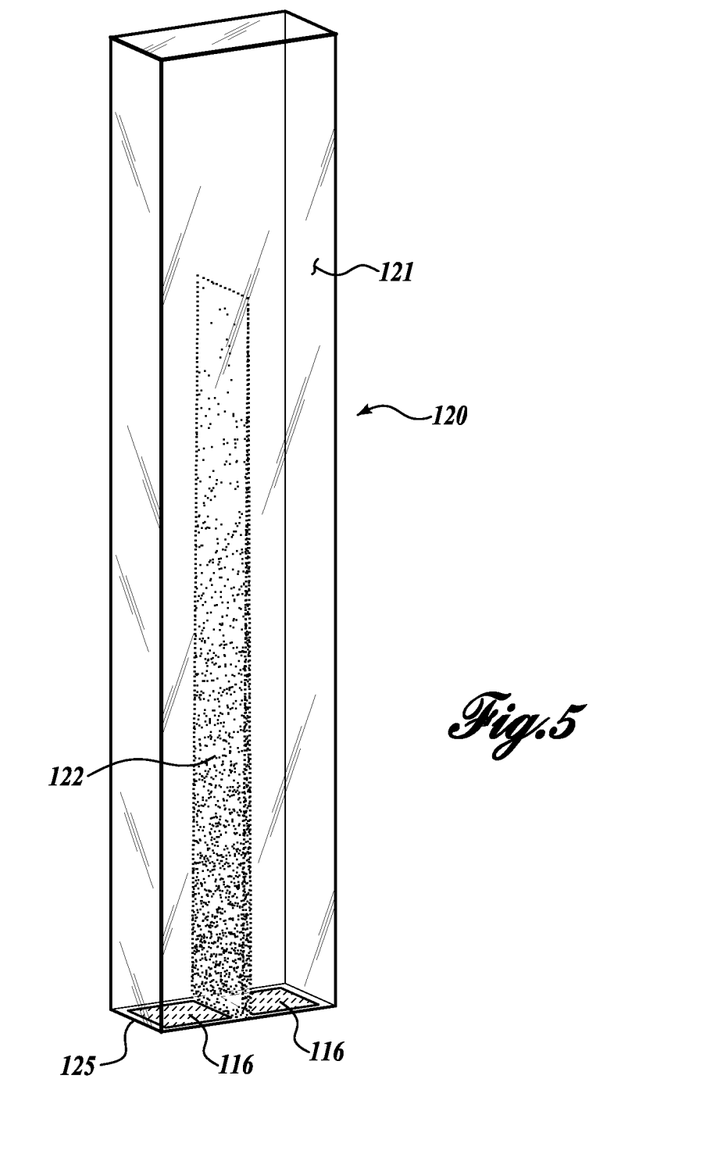
FIG. 5 is a perspective view of a depth-of-interaction monolithic crystal pair wherein an internal reflective feature is formed with graded density by subsurface laser engraving.

FIG. 5 illustrates another embodiment of an exemplary depth-of-interaction paired crystal detector 120 with a monolithic crystal 121. The crystal 121 is processed using SSLE to define a reflective internal boundary 122. In this embodiment the internal boundary 122 extends across the width of the crystal 121 for its entire length, rather than having a tapering shape. However, the density of the point-like defects that define the reflective boundary 122 varies in the longitudinal direction. In a particular embodiment, the density of the defects decreases continuously from the base of the boundary 122, such that the density of the defects near the photodetectors 116 at the face 125 of the crystal is much greater. Therefore, the amount of light that is shared between the two portions of the crystal 121 (the portions on either side of the internal boundary 122) varies along the length of the crystal 121. The depth of a scintillation event occurring in the detector 120 may therefore be estimated by comparing the light signal responses from the two photodetectors 116.

It is contemplated, however, that the concentration of defects may vary in a more complicated manner, for example, with a minimum defect density at an intermediate point along the length of the crystal. It will also be apparent from the present disclosure that the density of the defects may be varied on a shaped internal boundary such as that shown in FIG. 4.

Continuous Crystal without Discrete Barriers

In another embodiment of the present invention, a scintillation crystal is formed without reflective barriers that define separate crystal elements. As discussed in *cMiCE: a high resolution animal PET using continuous LSO with a statistics based positioning scheme*, and in U.S. Patent Application Publication No. 2010/0044571, referenced above, a continuous miniature crystal element (cMiCE) detector may be formed as a single slab of scintillator material (for example, LYSO), and the signals from an array of photodetectors on a face of the continuous crystal may be analyzed to estimate the three-dimensional location of a scintillation event within the crystal.

For example, some of the present inventors have developed a continuous miniature crystal element detector composed of a 50-mm×50-mm×8-mm slab of LYSO, coupled with a 64-channel, multi-anode, flat-panel photomultiplier tube. A statistics-based positioning algorithm analyzes the light response function from the array of photomultiplier tube channels to calculate the three-dimensional position of a scintillation event within the crystal.

Figure 6:
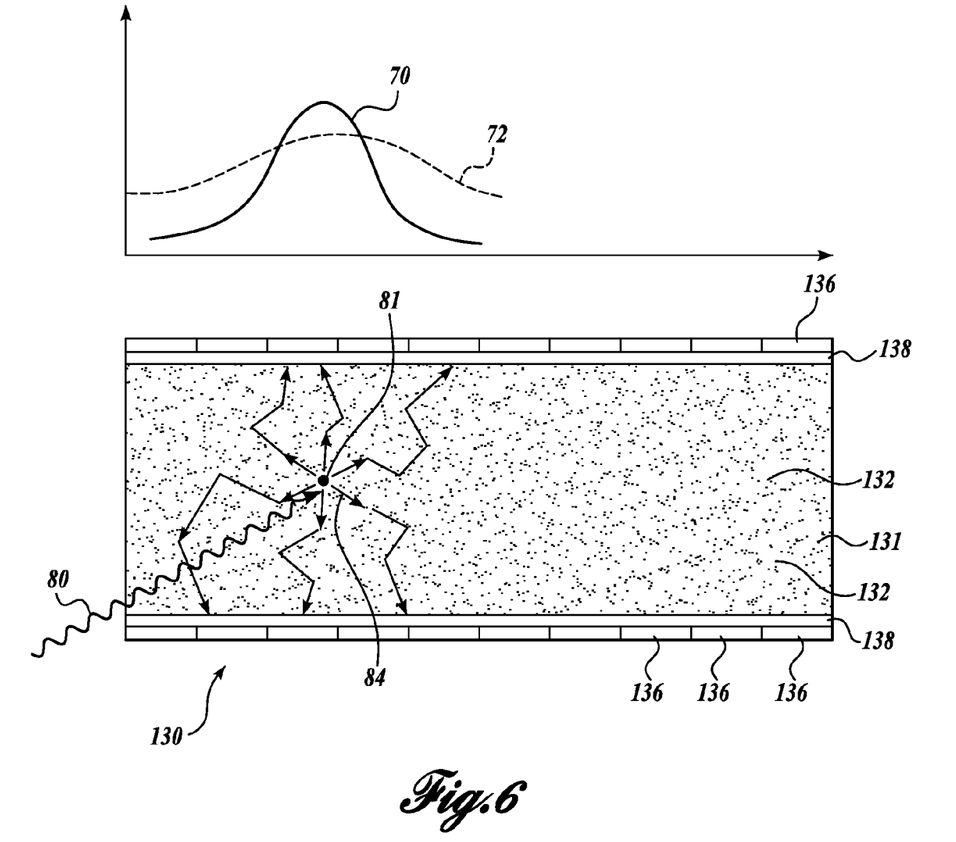
FIG. 6 is a perspective view of a scintillation detector with a continuous monolithic scintillation crystal having distributed point-like defects through the volume of the crystal that are formed by subsurface laser engraving.

A diagrammatic side view of a continuous crystal photon detector 130 in accordance with the present invention is shown in FIG. 6. In this embodiment a monolithic scintillating crystal 131 is shown with a pair of photosensor entrance windows or light guides 138 provided on opposite sides of the crystal 131, and a two-dimensional array of photodetectors 136 disposed on each of the light guides 138. The scintillating crystal 131 is configured with a plurality of point-like defects 132 that are produced by SSLE and distributed throughout the crystal 131. In the currently preferred embodiment the defects 132 are approximately uniformly distributed throughout the crystal, although it is contemplated there may be advantages to having non-uniformly distributed defects. For example, boundary issues may be mitigated by providing a more dense distribution of defects near the lateral boundaries of the scintillating crystal 131, e.g., to reduce the number of photons that escape without encountering one of the photodetectors 136.

Although in this embodiment separate photodetectors 136 are disposed on two opposite faces of the crystal 131, it is contemplated that the present invention may alternatively be practiced with different photodetector configurations. For example, an array of photodetectors 136 may be provided on only the entrance surface (or the surface opposite the entrance surface) of the crystal 131, with the opposing face roughed or otherwise configured to reflect photons. In another example, photodetectors may be provided on the lateral faces of the crystal 131 to capture information from photons escaping from the perimeter of the crystal 131.

Also diagrammatically illustrated in FIG. 6 is a gamma ray 80 that enters the crystal 131 and produces a scintillation event (at 81) that produces a large plurality of visible-wavelength scintillation photons 84 that are generally distributed uniformly in all directions. As illustrated, many of the scintillation photons 84 will reflect from defects 132 in the scintillation crystal 131 before exiting the crystal 131. The crystal 131 has a lateral dimension that is greater than its thickness, and therefore on average the scintillation photons 84 may encounter more defects 132 as they travel laterally through the crystal 131. The lateral spread of the light will therefore be preferentially attenuated by defects distributed throughout the crystal 131.

The distributed defects 132 will tend to sharpen the signal detected by the photosensors 136 from the scintillation photons 84, as illustrated by the graph associated above the detector 130. In the graph, the curve 70 illustrates diagrammatically a light distribution probability density function (PDF) for the scintillation event 81, as compared qualitatively with the light distribution PDF 72 that would be produced in a similar detector without the defects 132. It will be appreciated that the sharper PDF 70 resulting from the distributed defects in the crystal will increase the accuracy of the calculated three-dimensional estimation of the scintillation event location 81.

It will also be appreciated that although the point-like defects shown in FIG. 6 are disposed in the scintillation crystal 131, other optical elements in a scintillation detector may be similarly provided with point-like defects using SSLE to achieve a desired control of the scintillation light. For example, the light guides 138 may be fabricated with a distribution of defects to advantageously direct the scintillation light. In other embodiment of scintillation detectors, light guides and/or optical fibers are used to connect the scintillation crystal with the photodetectors. It is contemplated that such optical light guides may similarly be provided with defects to control and/or direct the scintillation light.

The examples described above and shown in the accompanying figures illustrate several embodiments for controlling the light output from a scintillation material to facilitate and improve detection of light resulting from scintillation events. As discussed above, the present method and devices provide advantages of improved performance, reduced cost of production, and simplified production.

Figure 7:
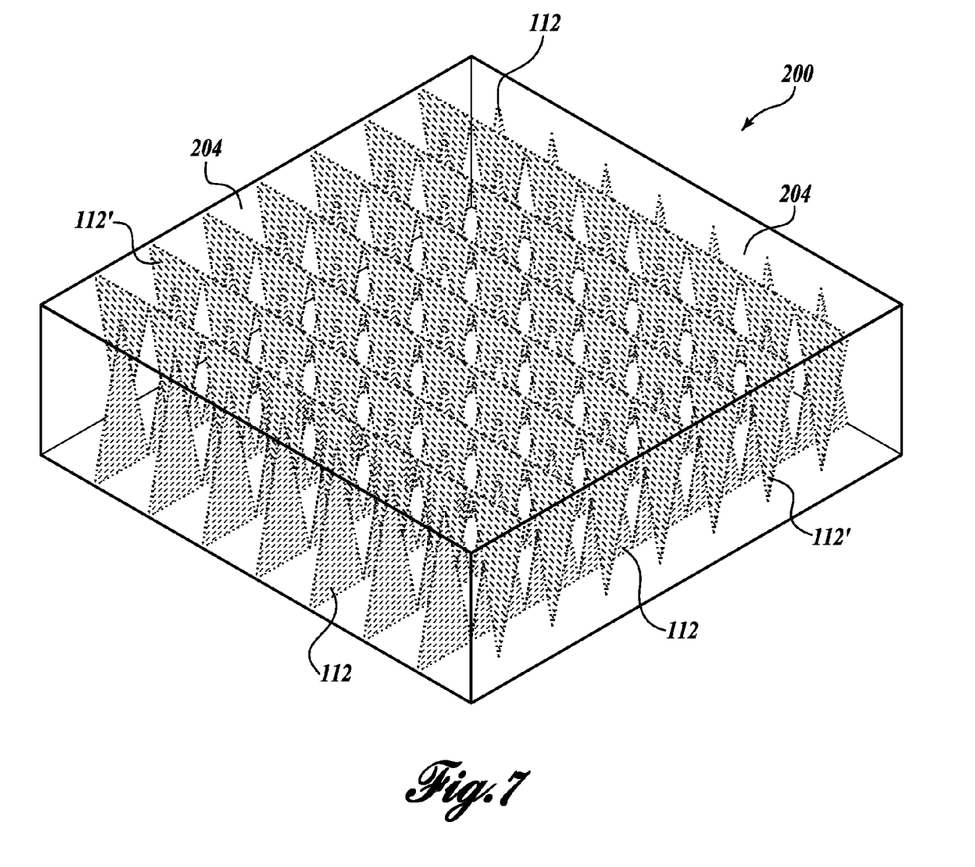
FIG. 7 is a perspective view of an embodiment of a monolithic scintillation block segmented into an eight by eight array of elements by a plurality of subsurface laser engraved shaped barriers shown in FIG. 4, the shaped barriers define reflective internal surfaces.

Also, while different aspects of the present invention are disclosed in separate embodiments, it is contemplated that the novel aspects may be combined in single apparatus. For example, it is contemplated that SSLE may be used to configure a monolithic crystal with optical barriers, such as barriers 102 shown in FIG. 2, and with partial barriers such as the boundaries 112 shown in FIG. 4, to provide a scintillation block 200 with an array of SSLE-generated optical barriers 112 and 112' as shown in FIG. 7, such that the crystal defines an array of depth-of-interaction crystal portions. Referring to FIG. 7, the triangular optical barriers 112 and 112' are perpendicular to the upper and lower faces of the block 200, and are configured to define a regular array of 64 transparent crystal elements 204. Alternatively, or in addition, the crystal portions may be provided with a smoothly distributed plurality of internal defects such as the defects 132 shown in FIG. 6.

While illustrative embodiments have been illustrated and described, it will be appreciated that various changes can be made therein without departing from the spirit and scope of the invention.

The embodiments of the invention in which an exclusive property or privilege is claimed are defined as follows:

1. A scintillation crystal-type radiation detector comprising:
    a transparent scintillator block formed from a scintillation material that is configured to interact with a high-energy photon in a scintillation event that releases a large number of low-energy photons; and
    a plurality of photodetectors positioned to receive at least some of the low-energy photons from the scintillation event and to produce corresponding output signals; and
    a computer system configured to receive the output signals from the plurality of photodetectors and to calculate the location of the scintillation event within the scintillator block;
    wherein the scintillator block includes a plurality of internal optical defects created in the scintillator block using subsurface laser engraving, and wherein the plurality of internal optical defects is configured to alter the path of at least some of the large number of low-energy photons within the scintillator block,
    wherein the scintillator block comprises at least one depth-of-interaction crystal element comprising a first portion having one of the plurality of photodetectors at a first end of the crystal element and a second portion having a different one of the plurality of photodetectors at the first end of the crystal element, and
    wherein the plurality of internal optical defects is disposed along a transverse plane that delineates the first portion from the second portion and the plurality of internal optical defects defines a triangularly shaped barrier along the transverse plane.

2. The radiation detector of claim 1, wherein the scintillation material comprises one of thallium doped sodium iodide, bismuth germinate, lutetium oxyorthosilicate, gadolinium orthosilicate, and cerium-doped lutetium yttrium orthosilicate.

3. The radiation detector of claim 1, wherein the plurality of photodetectors comprises components selected from photomultiplier tubes, avalanche photodiodes, Si-PIN photodiodes, silicon drift photodiodes, and silicon photomultipliers.

4. The radiation detector of claim 1, wherein the transparent scintillator block comprises a monolithic crystal, and further wherein the plurality of internal optical defects further define a plurality of reflective walls that define boundaries segmenting the monolithic crystal into a rectangular array of depth of interaction crystal elements.

5. The radiation detector of claim 1, wherein the plurality of photodetectors comprises a first array of photodetectors disposed on a first side of the scintillator block.

6. The radiation detector of claim 1, further comprising a transparent light guide disposed between the scintillator block and at least some of the plurality of photodetectors.

7. The radiation detector of claim 6, wherein the transparent light guide comprises a plurality of internal optical defects.

8. A scintillator for a radiation detector comprising a monolithic block of scintillation material having a plurality of subsurface laser engraved defects configured to interact with optical photons produced in a scintillation event occurring in the scintillator,
wherein the plurality of subsurface laser engraved defects defines a depth-of-interaction optical boundary in the scintillator, wherein the depth-of-interaction optical boundary extends partially through the scintillator along a plane, and further wherein the plurality of subsurface laser engraved defects defines a triangularly shaped barrier along the plane.

9. The scintillator of claim 8, wherein the plurality of subsurface laser engraved defects further defines a grid of internal shaped optical barriers that extends through a thickness of the scintillator.

10. The scintillator of claim 9, wherein the grid of shaped internal optical barriers defines a regular array of scintillator elements.

* * * * *